United States Patent [19]

Rösicke et al.

[11] Patent Number: 4,553,848

[45] Date of Patent: Nov. 19, 1985

[54] METHOD OF DETECTING AND EVALUATING PHOTOMETRIC SIGNALS AND DEVICE FOR CARRYING OUT THE METHOD

[75] Inventors: Bernd Rösicke, Mannheim; Rudolf V. Rosenbladt, Bad Homburg, both of Fed. Rep. of Germany

[73] Assignee: Boehringer Mannheim GmbH, Mannheim, Fed. Rep. of Germany

[21] Appl. No.: 413,291

[22] Filed: Aug. 31, 1982

[30] Foreign Application Priority Data

Sep. 30, 1981 [DE] Fed. Rep. of Germany ....... 3138879

[51] Int. Cl.⁴ .................... G01J 1/00; G01D 1/00; G01N 21/00; G01N 33/50
[52] U.S. Cl. ................................ 356/448; 356/226; 356/236
[58] Field of Search .............. 356/445, 446, 447, 448, 356/236, 215, 223, 226; 250/228, 214 C

[56] References Cited

U.S. PATENT DOCUMENTS

| | | | |
|---|---|---|---|
| 3,684,378 | 8/1972 | Lord | 356/447 |
| 3,738,755 | 6/1973 | Chaney et al. | 356/368 |
| 4,061,925 | 12/1977 | van der Gaag et al. | 250/553 |
| 4,124,301 | 11/1978 | Pocock | 356/442 |
| 4,201,472 | 5/1980 | Maeda | 356/226 |
| 4,320,970 | 3/1982 | Dowben et al. | 356/317 |
| 4,381,152 | 4/1983 | Riech et al. | 356/385 |

FOREIGN PATENT DOCUMENTS

| | | |
|---|---|---|
| 22524 | 1/1981 | European Pat. Off. . |
| 2158057 | 5/1972 | Fed. Rep. of Germany . |
| 140290 | 2/1980 | German Democratic Rep. . |
| 122936 | 9/1981 | Japan ...................... 356/448 |

OTHER PUBLICATIONS

Stark, Georg, "Fotometer für die Absorptionmessung im Durchlicht," *Electronik*, 1975, No. 12, pp. 65–68.

*Primary Examiner*—R. A. Rosenberger
*Attorney, Agent, or Firm*—Sprung Horn Kramer & Woods

[57] ABSTRACT

A method and device for detecting and evaluating the optical properties of a specimen, utilizing a light source that has alternating light and dark phases, a detector that picks up light from the light source by way of the specimen being examined, and a circuit that integrates and digitalizes the signals received from the detector, that includes an integrator, and that can be connected to the detector. The signals emitted from the detector are integrated both during at least part of the light phase and during at least part of the dark phase. The integral obtained during the dark phase is subtracted from that obtained during the light phase in order to determine the results. The integrator that is used to integrate the signals is used like an analog-to-digital converter of the double-integration type to convert the integral into a digital signal. To achieve maximum precision and simplicity in the integration and digitalization phase, each part of the light or dark phase is followed by a measurement-voltage period during which the signals coming from the detector are applied in sequence and with opposite mathematical signs to a single integrator. Integration is carried out over a whole number of measurement-voltage periods to form a total integral.

13 Claims, 5 Drawing Figures

METHOD OF DETECTING AND EVALUATING PHOTOMETRIC SIGNALS AND DEVICE FOR CARRYING OUT THE METHOD

BACKGROUND OF THE INVENTION

The present invention relates to a method for detecting and evaluating the optical properties of a specimen and a device for carrying out the method. The method uses a light source that has alternating light and dark phases, a detector that picks up light from the light source by way of the specimen being examined, and a circuit that integrates and digitalizes the signals received from the detector, with the signals emitted from the detector being integrated both during at least part of the light phase and during at least part of the dark phase, with the integral obtained during the dark phase being subtracted from that obtained during the light phase in order to determine the results, with a constant voltage of opposite polarity being applied to, and integrated down by, the integrator in order to convert the integral into a digital signal, and with a counting process triggered at the commencement of down-integration and stopped when a comparator value is attained.

The employment of photometric analysis, especially in the field of medicine and often utilizing test strips, is constantly increasing. Such procedures exploit chemical reactions that occur between the components of body fluids like blood or urine and reagents impregnated into certain reaction areas on the strip, which change color as a result. The changes in color can be quantitatively evaluated by appropriate procedures or devices. A reflected-light photometer for example can determine the reflectivity of such an area at one or more wavelengths of light subsequent to a reaction. In addition to this particular property of the specimen, a reference property and, if necessary, one or more additional specimen properties may have to be evaluated, depending on the given conditions.

Of course, types of analysis that do not employ strips also continue to be used in clinical chemistry. A change of color indicating a reaction that occurs within a more substantial volume of liquid may for instance need to be evaluated. Such methods employ transmitted-light photometers, and the invention may also be employed with this type of photometer.

The invention is preferably employed, however, with a reflected-light photometer, which is the embodiment that will be specified. This type of photometer includes an Ulbricht globe that uniformly distributes the light from a light source so that the test strip will be illuminated with diffused light passing through an aperture. The globe also contains two photodetectors, preferably photodiodes, one, the specimen-property detector, which detects light derived from the reaction area and the other, a reference-property detector, which detects light derived from an unaffected area of the inside surface of the globe. Since the detectors convert the photometric properties into very weak currents, of the order of 1 nA, the results must subsequently be amplified before being evaluated.

It is in clinical chemistry in particular that extraordinarily high demands are made on the detection and evaluation of photometric signals. Oscillations of 1 pA must be reliably detected to measure such weak currents with adequate resolution. There are, however, a number of sources of interference with this objective. They include problems like amplifier drift, superposed DC voltages (especially offset voltages from the components), relatively high-frequency noise voltages, low-frequency AC voltages, especially hum voltages spread with power-supply frequency, amplifier-input frequencies, and leakage or residual currents of various types, that are familiar in the electronics of detecting very weak signals.

Added to this are the sources of interference, especially from outside or extraneous light, that are especially typical in optical detection systems. Comparatively constant DC-voltage components are observed next to interference that is typical of extraneous light sources powered by the main supply equipment and operating at a conventional power-supply frequency of 50 or 60 Hz.

A number of methods of suppressing these sources of interference have been proposed. It is especially common to activate and deactivate the light sources at timed intervals, either by turning them on and off or by interposing and removing a screen. The signals obtained from the detector are then evaluated in the same way during both part of the light phase and part of the dark phase. Interference that contributes additively to the signal from the specimen-property detector and that changes slowly in relation to the rate at which the light source is activated and deactivated can then be substantially eliminated by subtracting the results obtained during the dark phase from those obtained during the light phase.

Methods that integrate the signal coming from the detector over a particular length of time are especially appropriate for suppressing high-frequency interference. Methods of this type will extensively suppress interference with frequencies that are much higher than the reciprocal of the period of integration.

A method and device of this type that combine both measures are known from U.S. Pat. No. 4,201,472. A detector is illuminated by a timed light source and the resulting signals are integrated during both part of the light phase and part of the dark phase. The integrals are evaluated immediately after each integration. This is done by applying a constant comparison voltage to the integrator and using it, analogously to an analog-to-digital converter that functions on the principle of double integration, for down-integration while simultaneously triggering a counting process. A comparator compares the output voltage of the integrator with a comparison voltage, usually a zero potential, and the counting is interrupted as soon as the output of the integrator reaches the zero potential. In the known method, the signals coming from the detector are evaluated during both the light phase and the dark phase, digitalized, and one result subtracted from the other to obtain a corrected value.

This known method, however, is still not completely satisfactory even though it eliminates both high-frequency interference as well as some of the low-frequency interference. Circuitry that will provide satisfactory precision is relatively expensive because the light source must be activated and deactivated fairly rapidly to suppress relatively high-frequency oscillations in the signal. This will leave a comparatively short time for integration during both the light and the dark phases, although the resolution of an analog-to-digital converter that operates according to the double-integration principle is to a large extent determined by maximum available down-integration time at a given counter rate and switching speed. If down-integration time is very short, the only solution is to employ correspondingly rapid components, which will make the device too expensive.

SUMMARY OF THE INVENTION

The object of the present invention is to provide a method of the type described that will simply and inexpensively suppress such errors and allow high resolution and precision. It should eliminate the need for expensive alignment devices, which as a rule require specialized knowledge and care, so that equipment operating in accordance with the invention will be inexpensive to manufacture and maintain.

The invention achieves these objectives with an integration and digitalization stage which comprises one or more measurement-voltage periods each of which includes a light and a dark phase and during which the signals coming from the detector are applied in sequence and with opposite mathematical signs to a single integrator, in which the parts of the light and dark phases are equal in length, and in which integration is carried out over a whole number of measurement-voltage periods to form a total integral that is then digitalized by the same integrator.

Although it is possible for integration to be carried out during both the total light phase and the total dark phase, it is preferable not to integrate over the course of a delay that occurs during the first part of both the light phase and the dark phase. This is because the detector signal or output voltage will overshoot at the beginning of the light phase as a result of heating-up processes that occur within the light source, which is specifically a light-emitting diode (LED). Similarly, relaxation effects that occur in the detector, which will preferably be a photodiode, at the beginning of the dark phase will delay the reduction of the signal. These temperature-dependent effects, which are very difficult to determine quantitatively, will not therefore be integrated during the delays but will be faded out, so to speak. Other transient processes however will also be faded out.

Integration in accordance with the invention over a sequence of several light and dark phases without intermediate digitalization will allow a longer integration time and relatively rapid timing of the light source. A long integration time will reliably eliminate even relatively low-frequency high-frequency interference and rapid timing of the light source will ensure the elimination of even comparatively rapidly changing DC components. Since digitalization will be necessary only after several integrations, digitalization time can also be relatively long, leading to high resolution with cost-effective components. The invention achieves these advantages with extremely simple means and hence at very low cost.

Integration time depends, for a given light-source timing rate and hence length of the measurement-voltage periods, on the number of measurement-voltage periods that are required for integration. This is preferably greater than 1, with an upper limit determined essentially only by the maximum amount of time that is available for one measurement.

To reliably suppress interference that is synchronous with the power-supply frequency as well, it is preferable to make the measurement-voltage period an even-number multiple of that of the power-supply frequency. This will make the interference show up in the same way in both the light and the dark phases, so that it can be eliminated in accordance with the invention by applying the signal coming from the detector during part of the light phase to the integrator with a mathematical sign that is the opposite of that with which it is applied during the same part of the dark phase.

Any parts of the light and dark phases can in general be employed in accordance with the invention for integration. It is only essential that they be equally long so that the corrected value will correspond to the measured value.

It is especially preferable in accordance with the invention to employ in addition to the system that consists of the light source, the specimen, and the detector, a reference-property detection system that consists of the same light source, a reference area, and a reference-property detector. A second photodiode in the integration globe of a reflected-light photometer is preferable. The invention, however, is not restricted to such a design and also comprehends those cases in which one detector is utilized as both a specimen-property and a reference-property detector. The advantages of the invention can be exploited especially effectively if, when a reference-property detection system is employed, the signal from the reference-property detector is alternated with the signal from the specimen-property detector and evaluated by one and the same measurement and integration circuit. In this case, the integration and digitalization phase associated with evaluation of the signal from the reference-property detector will be the exact equivalent of that associated with evaluation of the signal from the specimen-property detector, and the results of total integration will be derived by constructing a quotient. It must be emphasized that switching back and forth between the specimen-property detector and the reference-property detector can be either electrical, which is especially the case when two separate detectors are employed, or optical. Optical switching can be accomplished with optical devices like mirrors, light guides, etc. that will conduct the light alternately from the specimen-property detection system and the reference-property detection system to the preferably single photodetector, which will in this case serve as both specimen-property and reference-property detector. These preferred means will eliminate all sources of error that change slowly in relation to switching back and forth between the specimen-property detection system and the reference-property detection system and make for linear error contribution. These include in particular long-term changes in the components that determine electronic amplification and long-term changes in photodetector sensitivity.

One preferred embodiment of the invention carries out additional zero compensation to eliminate zero errors, especially those that occur as the result of integrator offset, which are not generally determined by the invention in its overall form. In this case, another integration and digitalization phase, in addition to those already described in relation to the signals from the specimen-property detector and reference-property detector, is carried out that is absolutely identical with them except that the signal applied to the specimen-property integration and digitalization circuit is a zero signal instead of a signal coming from a detector. This provides a third total integral that is employed as a zero value and is utilized in digitalized form to correct digitalized total integrals derived from the detectors.

The device that carries out the method in accordance with the invention has a light source for illuminating the specimen and a specimen-property detector that picks up light coming from the specimen and releases an appropriate analog signal. The analog signal is applied to a specimen-property integration and digitalization circuit that, since it includes an integrator, can measure, integrate, and digitalize the signal as described above. An interruptor is associated with the light source and activates and deactivates it at timed intervals to generate specimen-property voltage periods in the detector. The integrated signal is digitalized with a down-integration switch that can apply to the integrator a constant voltage that is derived from an appropriate voltage source and that has a polarity that is the opposite of that of the analog signal. There is also a comparator of the type conventional for digitalization circuits that function in accordance with the principle of double integration. The comparator compares the voltage leaving the integrator with a reference voltage. The signal coming from the comparator is applied to a gate circuit that also receives a signal from another component of an appropriate type at the instant at which the down-integration voltage is applied to the integrator. This signal causes the gate circuit to extract pulses from a clock and forward them to a counter when the output voltage from the integrator is more powerful than the comparator voltage. Digitalizing stops when this state is achieved.

The objectives described above are achieved with a device of this type that employs inexpensive circuitry, that is reliable, and that is composed of a relatively small number of standard components. This is the result of polarity reversing switch between the specimen-property detector and the integrator that is synchronized with the light-source interruptor and that applies the signal coming from the detector to the integrator both when the light source is activated and, with opposite polarity, when the light source is deactivated. This device incorporates the method in accordance with the invention as described above.

Some preferred embodiments of the invention are also the objects of the invention and are disclosed hereinafter. They will be specified with reference to the drawings. These embodiment represent a system that allows an extremely high level of measurement precision without using components that are difficult to obtain. The circuitry requires no calibration during manufacture or maintenance and is stable for an unusually long time.

Further advantages and characteristics essential to the invention will be evident from the following specification with reference to the drawings, in which

DETAILED DESCRIPTION OF THE INVENTION

Figure 1:
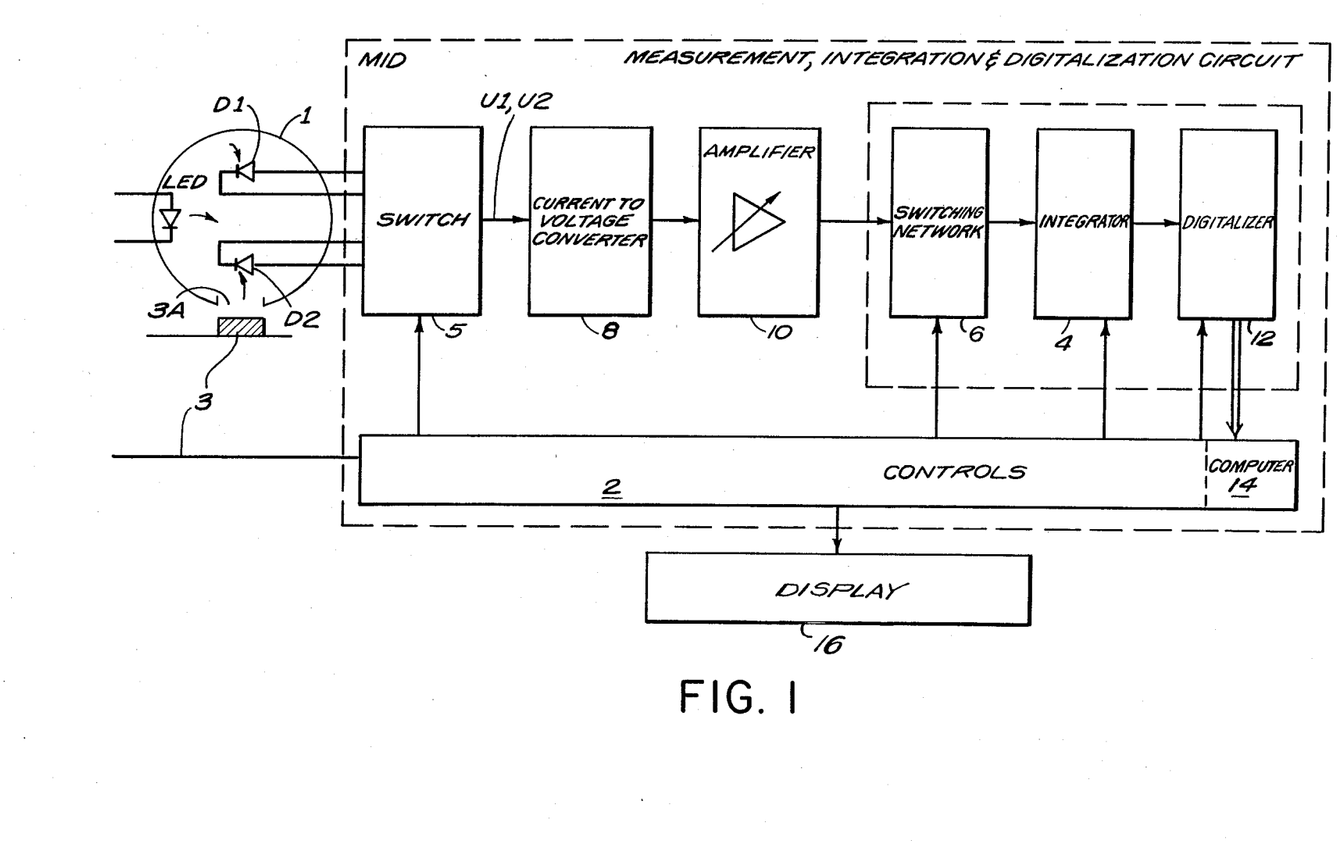
FIG. 1 is a block diagram of a device for carrying out the method in accordance with the invention.

The block diagram in FIG. 1 schematically shows and Ulbricht globe 1 with a light source LED and two detectors D1 and D2. The light from source LED is uniformly distributed by a known process inside the Ulbricht globe in such a way that the specimen, which may for example be a test strip 3, is illuminated with diffused light through an aperture 3A. The two detectors D1 and D2 are diodes that are positioned inside the globe in such a way that the only light that detector D2, which is the specimen-property detector and is aimed at the test strip, can pick up is the light coming from the strip, whereas the only light that detector D1, which is the reference-property detector, can pick up is that derived from an unaffected area of the inside surface of the globe. Light source LED, the surface of test strip 3, and specimen-property detector D2 make up a specimen-property detection system. The same light source LED, an appropriate area of the inside surface of the globe, and reference-property detector D1 make up a reference-property detection system.

Controls 2 activate and deactivate light source LED at timed intervals to generate a light phase, during which the source emits light, and a dark phase, during which no light is emitted and may include a software controlled microprocessor. The light and dark phases are produced by a series-wired switch S1 that turns source LED on and off (cf. FIG. 5).

The properties detected by the detectors are converted into appropriate signals. These signals are evaluated by a measurement, integration, and digitalization circuit MID, which contains in sequence a switch 5, a converter 8, an amplifier 10, a switching network 6, an integrator 4, a digitalizer 12, and controls 2.

Switch 5 has two inputs and, subject to controls 2, forwards signals from either reference-property detector D1 or specimen-property detector D2 as desired to downstream converter 8.

Converter 8 converts the weak current from the detectors into a voltage that is amplified by a downstream amplifier 10.

The signal emitted by amplifier 10 is supplied through a switching network 6 to an integrator 4. Controls 2 synchronize switching network 6 and integrator 4 in such a way that integrator 4 integrates specimen-property or reference detection signals U1 and U2 and interference 01 and 02 in the three sequential stages of measurement, integration, and digitalization, which will be described in more detail later. It is significant that one sole integrator 4 determines that mean signal value, compensates for interference values, especially offset voltages, and, in conjunction with downstream digitalizer 12, converts analog signals into digital signals and performs zero compensation, with controls 2 governing the individual stages of the process.

The digital values occur in the counter in digitalizer 12, whence they are supplied to a computer 14 in controls 2 that calculates the results, which are displayed on a display 16.

Figure 2:
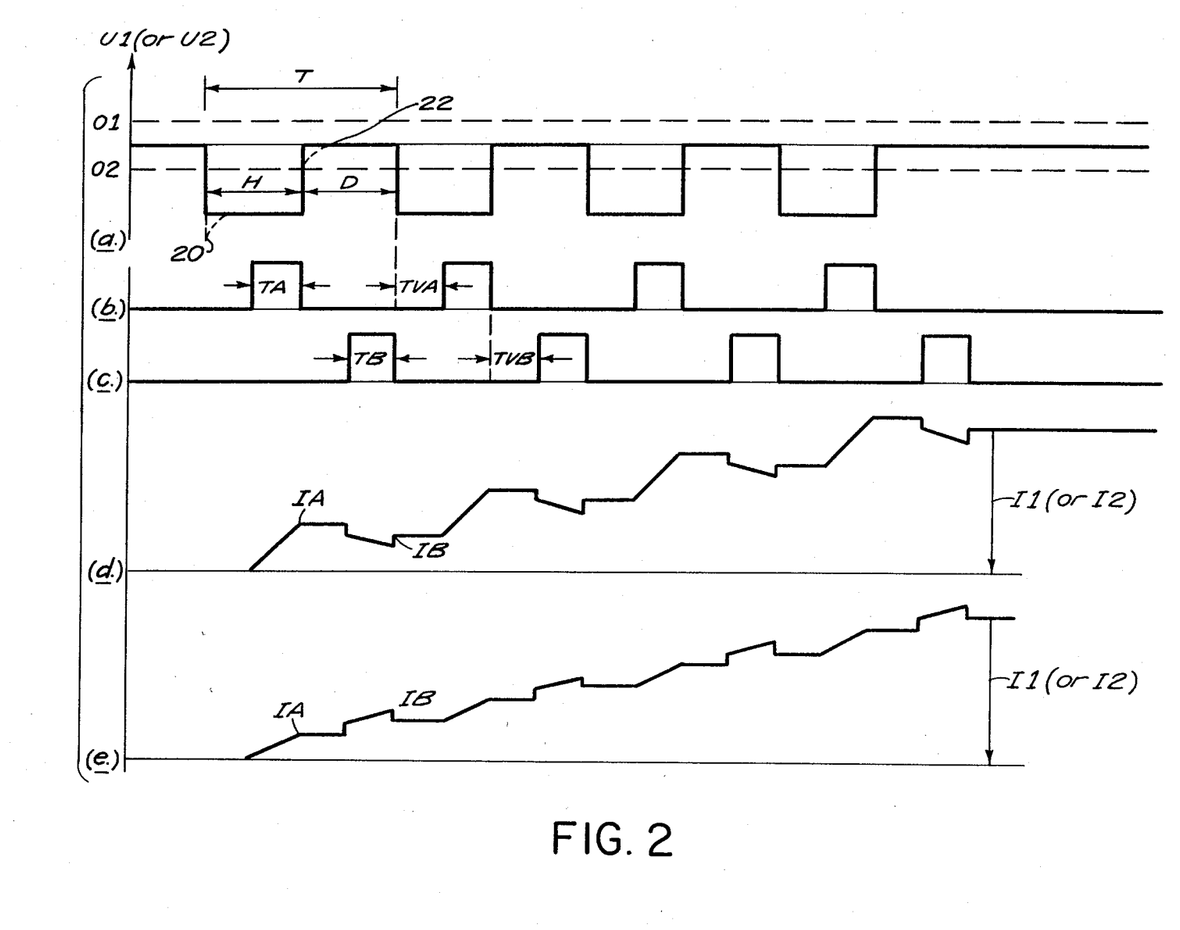
FIG. 2 is a timing diagram illustrating the activity over time of the integral I1.

FIG. 2 illustrates various timing graphs that help to explain the activity of an integral I1 over time.

In graph a, signal U1 is represented as a negative voltage. Each light phase H is associated with a voltage, which drops to zero during a dark phase D. It is preferred for the light phase H and dark phase D to last for a time T that equals 200 msec. The invention thus makes it possible to compensate even for superposed alternating voltages with fundamental frequencies of 50 or 60 Hz and thus prevent the beats that they provoke. The signal U1 will, at the beginning of a light phase H, overshoot as indicated by the broken line 20. This overshooting is caused in particular by the temperature of light source LED. At the beginning of dark phase D the value will drop to zero after a certain delay as indicated by the dotted and dashed line 22. This is the result of relaxation on the part of detector D1, which is a photodiode.

To eliminate these transients as well as other on and off switching transients, integration does not begin until after the delays TVA and TVB shown in graph b and c. Graph a also shows a positive 01 and a negative 02 offset voltage. How these two types of offset voltages can be eliminated will be explained. Four periods (of duration T) of a measurement voltage U1 timed with a frequency of 5 Hz are also shown.

Figure 5:
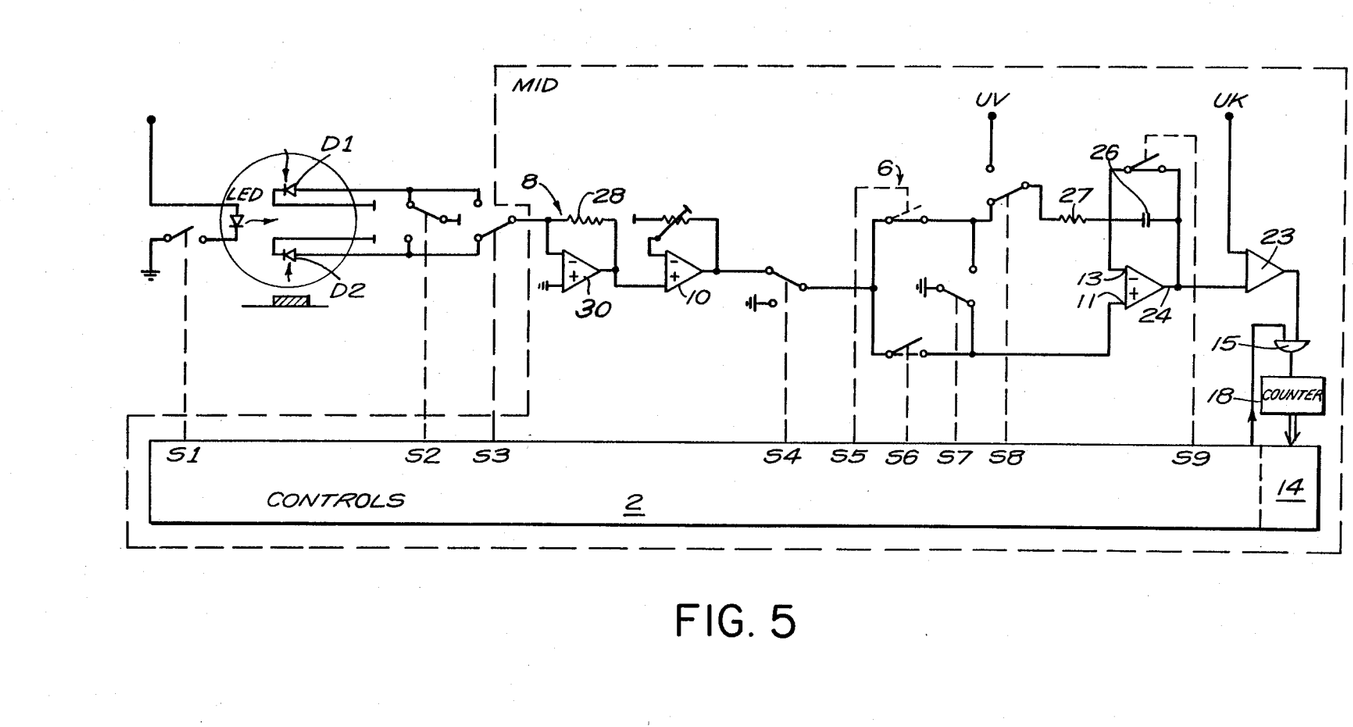
FIG. 5 is a circuit diagram illustrating the principle of one preferred embodiment of the circuitry.

Graph b shows the pulses that control up-integration of the value together with the positive or negative offset voltage. These pulses begin following the delay times TVA after the commencement of light phase H, with a given integration time TA of 50 msec. Switch S5 is, as indicated in FIG. 5, closed during integration time TA, so that up-integration can be carried out.

Graph c shows the pulses during dark phase D, with down-integration being carried out over integration time TB. Each pulse begins following a delay time TVB after the commencement of dark phase D. Note especially that integration times TA and TB are equal in length. The integration times and the delay times TVA and TVB are all 50 msec long. Although integration times TA and TB, however, must be equally long, delay times TVA and TVB may in special cases differ, either one from the other or from integration times TA and TB. Since a test-voltage period is obtained as the sum of integration times TA and TB and possibly of several delay times as well, it is also possible for the light and dark phases to be of different lengths. The present embodiment, in which the delay times TVA and TVB are equally long and as long as integrations times TA and TB, and in which the light phases H and dark phases D are hence equally long, the circuitry is especially simple and the pulses are easy to derive from a fundamental frequency, an oscillator frequency for example. Switch S6, as indicated in FIG. 5, is closed during integration times TB.

Graph d illustrates the activity over time of the integral I1 for the offset voltage 01. Integral IA occurs at the end of the first integration time TA and remains during the subsequent delay time TVB, during which no integration is carried out. Another integration occurs for integration time TB during dark phase D, with down-integration occurring as determined by the sign reversal carried out by the integrator. Since no detection value is present during the dark phase, but only offset voltage 01, a corresponding value IB is subtracted. Since integration times TA and TB are, in accordance with the invention, of equal length, the integral that occurs at the end of dark phase D will no longer be contaminated by offset voltage 01. Since these processes are on the whole carried out during four periods T, at the end of which the analogous total integral I1 will appear at the output of the integrator, the above-mentioned offset compensation will make the total integral correspond to the signal U1.

Graph e shows the activity over time of the integral for the case that a negative offset voltage 02 is superposed on the value. Since the amount from the negative signal U1 and the likewise negative offset voltage 02 is now lower than in the case discussed above, integration will also occur during integration time TA with a slope that is less steep. Only offset voltage 02 is now integrated during integration time TB of the dark phase, so that the integral will now increase with a correspondingly flatter slope, considering the mathemetical sign. Thus, offset voltage will be compensated for by the end of the first cycle.

The above discussion proceeds from the assumption that offset voltage will remain constant during at least one measurement voltage time T. As long as this assumption is complied with, compensation will be satisfactory. It is preferable to keep the periods as short as possible to make allowance for the assumption in practice as well. The short integration time that is as a result of these short periods available for establishing a mean value can be compensated for in accordance with the invention by carrying out a number of periods in sequence.

One type of periodic interference that is superposed on the offset, that is particularly significant in practice, and that can be compensated for in accordance with the invention is what is called power-line hum. It oscillates at power-supply frequency and can be caused in the case of photometry either optically by the scattering of light from light sources working off the main power supply or by electromagnetic activity in the electronic circuit. This interference will be optimally compensated for during a period lasting $T=H+D=TVA+TA+TVB+TB$ if $T=2m\times T_N$, where m is a whole number and $T_N$ the length of a period with power-supply frequency. If a superposed alternating voltage of 50 or 60 Hz is to be compensated for, the shortest time T will be 40 or 33 1/3 msec respectively. If these two interference frequencies with a common time T are to be eliminated, the shortest suitable time T will be 200 msec.

A comparison of graphs d and e will immediately show that the same total integral I1 will always be available at the end of the n=4 periods regardless of the mathematical sign of the offset voltage.

Figure 3:
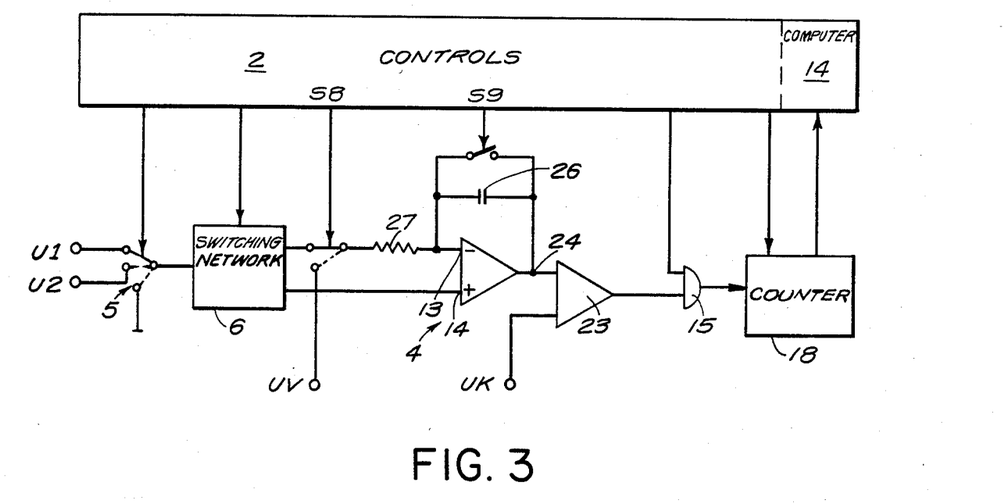
FIG. 3 is a block diagram illustrating the analog-to-digital conversion circuitry.

FIG. 3 is a schematic diagram of an analog-to-digital converter for the signals U1 and U2. The converter 8 and amplifier 10 from FIG. 1 are not shown for the sake of clarity. Switch 5, which is governed by controls 2 can connect either signal U1 or U2 to switching network 6 as desired. It can also ground the input of switching network 6. Switching network 6 and subsequent integrator 4 can, subject to controls 2, carry out the zero compensation and mean determination discussed above. Assume, then, that there is an analog integral I1 at the output 24 of integrator 4. Now, when switch 5 switches signal U2 through, there will be a corresponding integral I2 at output 24. When each of these integrals is to be converted from an analog to a digital value (integral I1 will be dealt with alone at first for the sake of clarity), activation of down-integration switch S8 will provide a down-integration voltage UV at the inverting input 13 of integrator 14. An integration capacitor 26 is wired between input 13 and output 24. A comparator 23 with an output that leads through an AND gate 15 to a counter 18 is wired downstream of integrator 4. There is a comparator value UK in the form of a direct-current voltage at another input to comparator 23. When switch S8 switches over, and, hence, when down-integration voltage UV is applied, controls 2 supply a counting pulse through gate 15 to counter 18, which is immediately enabled. It is practical for the counter to have been zeroed so that it will now count throughout the pulse. Down-integration voltage UV will decrease the voltage at the output of integrator 24. When this voltage attains comparator value UK, which in accordance with the invention has a mathematical sign that is the opposite of the voltage at the integrator output gate 15 will close and no more counting pulses can reach counter 1. The counter state, which is the digital value Z1, will not, however, directly equal signal U1, but will be contaminated by various interference values, among which may be mentioned here in particular the offset voltages of integrator 4 and comparator 23, so that total integration time and the integration-time constants with respect to the capacity of capacitor 26 and the ohmic resistance value of the resistor 27 that is upstream of integrator 4 must also be taken into consideration.

Digital value Z1 will also be affected by the parameters of comparator value UK and down-integration voltage UV. It need hardly be mentioned that similar interference and errors occur when constructing a digital value for signal U2. Switch S5 is switched to ground potential to determine a digital zero value Z3 in relation to this interference and these effects. The digital values Z1 or Z2 for signals U1 and U2 are determined in the same way during two integration and digitalization phases. The zero value Z3 is determined in another, third, integration and digitalization phase that is timed or governed by the controls in the same way as the other two phases except that switch S5 applies the zero potential to the input of switching network 6. At the end of each phase the digital values Z1 and Z2 and the zero value Z3 is entered in computer 14. Computer 14 then easily constructs the quotient of the differences between digital value Z2 and zero value Z3 and between digital value Z1 and zero value Z3. This quotient is the desired result from the ratio between specimen-property signal U1 and reference signal U2.

Figure 4:
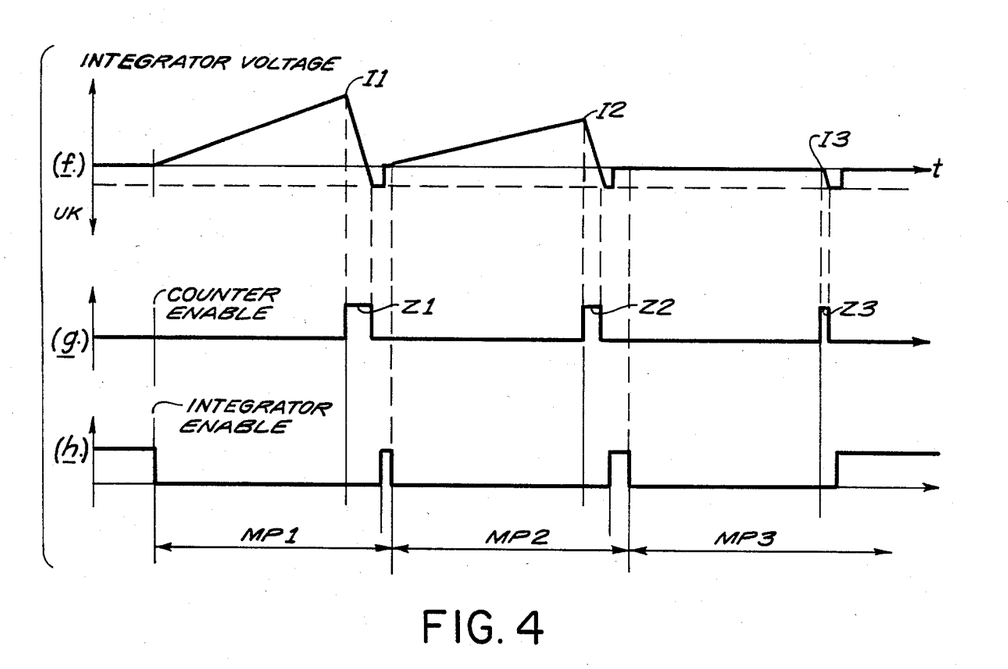
FIG. 4 is a graph illustrating the activity over time of the integral and the formation of corresponding digital values during 3 integration and digitalization phases of one complete determination process.

FIG. 4 illustrates the activity of the integrals over time and the construction of corresponding digital values during one complete detection process throughout three integration and digitalization phases MP1, MP2, and MP3. Graph f shows schematically the increase of the voltage of the integrator at its output 24. The increase in voltage subsequent to the enabling of the integrator is depicted as linear for the sake of clarity. Actually, however, the voltage will increase irregularly as in FIG. 2. When the n measurement-voltage periods mentioned above are finished, total integral I1, which corresponds to reference signal U1 will occur first. Down-integration for analog-to-digital conversion is subsequently carried out during phase MP1, with the counter also being enabled simultaneously with the beginning of down-integration and with the application of down-integration voltage UV as shown in Graph g. The counter stops when the integrator voltage attains the negative comparator value UK. The digital value Z1 is constructed during counter start. Subsequently, the integrator is zeroed as in graph h, with switch S9 being closed as shown in FIG. 5. Signal U2 is up-integrated at the beginning of second integration and digitalization phase MP2 to construct total integral I2 analogously. During the subsequent down-integration the counter is again enabled and a digital value Z2 corresponding to integral I2 is constructed. Since integral I2 is smaller than integral I1, the counter will be enabled for a shorter time with the consequence that the counter state and digital value Z2 will be lower. A third measurement phase MP3 is carried out in accordance with the invention to determine the zero value. Since the integrator input is now at zero potential, integral I3 will now essentially equal zero. It is also possible, however, because the integrator offset voltage differs from zero, for an integral I3 that differs from zero to appear. All interference, like integrator offset voltage, integrator offset current, etc., will, however, easily be detected when integral I3 is integrated down to comparator value UK and zero value Z3 is constructed and can be subtracted digitally from specimen-property value Z1 and reference value Z2.

From FIG. 4 it will be evident that the preferred polarity of comparison voltage UK will be different from zero and opposite to that of the analog signal from detector D1 or D2. This will ensure a switching edge even when the total integral to be digitalized is extremely small, as is often the case during integration and digitalization phase MP3 in particular. Furthermore, since total integrals I3 of both polarities can appear during integration and digitalization phase MP3, there could be a case in which no switching edge would result if a comparison voltage that exactly equalled zero were selected. A comparison voltage that is not equal to zero results in a counter state Z1, Z2, and Z3 that is too high. Since, however, counter state Z3 is always subtracted from counter states Z1 and Z2 to obtain the results and since the counter-state error is always of the same size, this error will again be eliminated.

FIG. 5 is a simplified diagram of preferred circuitry. To avoid repetition the components specified with reference to the previous figures will not be discussed further and the text above should be consulted for their arrangement and function. Basically, controls 2 activate switches S1 through S9 to produce the timed periods and phases specified above. Switch S1 is in series with light source LED and controls light and dark phases H and D. Switches S2 and S3, which correspond to the switch 5 specified above, are wired downstream from detectors D1 and D2 and can connect either of them to converter 8. The current-voltage converter 8 contains an operational amplifier 30 that is wired with a high-ohmage resistor 28. An amplification drift may occur as the result of aging and of the temperature coefficient of resistor 28. The effects of such an amplification drift are largely eliminated because of the switching of detectors D1 and D2 explained above. Since in fact there is in accordance with the invention only one single measurement, integration, and digitalization circuit MID, the amplification drifts for both signals U1 and U2 will remain practically the same during the relatively short measurement time of a few seconds.

Changes over the long term will preferably be eliminated by constructing a quotient of the specimen-property and reference signals. An amplifier 10 is also positioned downstream from converter 8. The amplifier output is connected through the switching network 6 with its switches S4 through S8 to integrator 4. Switch S4 (a zero switch) switches to ground potential in order to determine zero value Z3 during the further, third, integration and digitalization phase MP3. During phases MP1 and MP2, switch S4 is in the position illustrated. Switches S5 and S6 apply signals during the light or dark phase or apply the ground potential to either the inverting 13 or the non-inverting 11 input of integrator 4 so that the appropriate signal or interference will be integrated up during the light phase but only the interference will be integrated during the dark phase and subtracted with the correct mathematical sign from the previously obtained integral as a result of change in polarity.

Another switch S7 is synchronized with switches S5 and S6 and applies ground potential to the input of the integrator, which is not connected to the signal, the three switches S5, S6, and S7 thus forming a pole-changing circuit. Switch S8 (an down-integration switch) supplies the down-integral UV to the integrator at the beginning of down-integration to convert from analog to digital. Switch S9 is connected in parallel to integrator 8 or to its capacitor 26 and rezeroes integrator 4 before the commencement of each measurement phase. Switch S9 opens to enable the integrator. Comparator 23, and, through AND gate 15, counter 18 are positioned downstream of integrator 4. See the above with reference to FIG. 3 for an explanation of their function.

The circuitry in accordance with the invention is extremely simple because integrator 4 is employed not only for zero compensation and mean determination but also for analog-to-digital conversion and to determine the zero value. It is emphasized once again in particular that this design employs only one single measurement and integration system that is timed in a very simple way by controls that include a computer.

It will be appreciated that the instant specification and claims are set forth by way of illustration and not limitation, and that various modifications and changes may be made without departing from the spirit and scope of the present invention.

What is claimed is:

1. In a method for detecting and evaluating the optical properties of a specimen including producing alternating light and dark phases from a light source, detecting light from the light source by way of an analog specimen to produce a signal, integrating and digitalizing the signal from the detector during the light phase and during the dark phase and subtracting the integral obtained during the dark phase from that obtained during the light phase, the improvement wherein the steps of integrating and digitalizing comprise:

forming a first total integral in a first state including a whole number of measurement voltage periods each including one light and one dark phase comprising the steps in each period of integrating the detected signal during a part of the light phase with a single integrator and integrating the detected signal with the reversed polarity with the same single integrator during a part of the dark phase equal in length to the part of the light phase and digitalizing the total integral with the same single integrator.

2. The method according to claim 1, wherein the steps of integrating the detected signal during the light and dark phases each comprise delaying the start of the integrating by the same predetermined time after the start of the light and dark phases.

3. The method according to claim 1 or 2, wherein the whole number of measurement-voltage periods is greater than 1.

4. The method according to claim 1 or 2, further comprising energizing the light source with an ac power supply and wherein the length of the measurement-voltage period is an even multiple of the period of the power supply frequency.

5. The method according to claim 1, further comprising detecting light from the light source by way of a reference light detector and producing a reference signal and wherein the steps of integrating and digitalizing comprises forming a second total integral of the reference signal in a second stage equivalent to the first stage and using the same single integrator, digitalizing the second total integral of the reference signal with the same single integrator and forming a quotient of the digitalized total integrals from the two stages.

6. The method according to claim 5, further comprising providing a zero signal to the same single integrator and wherein the steps of integrating and digitalizing further comprises forming a third total integral of the zero signal in a third stage equivalent to the first stage and using the same single integrator, digitalizing the third total and correcting the first and second total integrals with the digitalized third total integral before forming the quotient.

7. In a device for detecting and evaluating the optical properties of a specimen having a light source, means for producing alternating light and dark phases from a light source, first means for detecting light from the light source by way of a specimen and produce an analog signal, an integrating and digitalizing circuit receptive of the signal from the detecting means during the light phase and during the dark phase means for subtracting the integral obtained during the dark phase from that obtained during the light phase, the improvement wherein the integrating and digitalizing circuit comprises: means forming a first total integral during first stage including a whole number of measurement-voltage periods each including one light and one dark phase a single integrator and means synchronized with the means producing the light and dark phases for applying in each period the detected signal during a part of the light phase to the input of the single integrator and for applying the detected signal with the opposite polarity during a part of the dark phase equal in length to the part of the light phase to the input of the single integrator and means for digitalizing the total integral comprising the single integrator.

8. The device according to claim 7, wherein the means for applying the detected signal during the light and dark phases comprises means for delaying the start of the integrating by the same predetermined time after the start of the light and dark phases.

9. The device according to claim 7 or 8, wherein the whole number of measurement-voltage periods is greater than 1.

10. The device according to claim 7 or 8, further comprising means for energizing the light source comprising an ac power supply and wherein the length of the measurement-voltage period is a even multiple of the period of the power supply frequency.

11. The device according to claim 7, further comprising second means for detecting light from the light source as a reference and for producing a reference signal and wherein the integrating and digitalizing circuit further comprises means forming a second total integral of the reference signal during a second stage equivalent to the first stage and comprising the same integrator, means for digitalizing the second total integral of the reference signal with the same single integrator and means forming a quotient of the digitalized total integrals.

12. The device according to claim 11, further comprising means for applying a zero signal to the same single integrator and wherein the integrating and digitalizing circuit further comprises means forming a third total integral of the zero signal during a third stage equivalent to the first stage and comprising the same single integrator, means for digitalizing the third total integral and means for substracting the digitalized third total integral from the digitalized first and second total integrals and forming the quotient of the difference between the first total integral and the third total integral and of the difference between the second total integral and the third total integral.

13. The device according to claim 12, wherein the first and second detecting means comprises photodiodes and wherein the integrating and digitalizing circuit includes a current to voltage converter.

* * * * *